United States Patent
Karasawa et al.

(10) Patent No.: US 10,495,595 B2
(45) Date of Patent: Dec. 3, 2019

(54) GAS SENSOR DEVICE, GAS MEASUREMENT METHOD, AND GAS MEASUREMENT DEVICE

(71) Applicant: FUJITSU LIMITED, Kawasaki-shi, Kanagawa (JP)

(72) Inventors: Kazuaki Karasawa, Hadano (JP); Michio Ushigome, Atsugi (JP); Satoru Momose, Atsugi (JP); Ryozo Takasu, Isehara (JP); Osamu Tsuboi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 391 days.

(21) Appl. No.: 15/381,074

(22) Filed: Dec. 15, 2016

(65) Prior Publication Data

US 2017/0254767 A1 Sep. 7, 2017

(30) Foreign Application Priority Data

Mar. 3, 2016 (JP) .................. 2016-041476

(51) Int. Cl.
*G01N 27/12* (2006.01)
*G01N 33/00* (2006.01)
*G01N 27/407* (2006.01)

(52) U.S. Cl.
CPC .......... *G01N 27/12* (2013.01); *G01N 27/4077* (2013.01); *G01N 33/0009* (2013.01); *G01N 33/0027* (2013.01); *G01N 33/0054* (2013.01); *Y02A 50/246* (2018.01)

(58) Field of Classification Search
CPC .......... G01N 33/0009; G01N 33/0027; G01N 27/4077; G01N 27/12; G01N 33/0054
See application file for complete search history.

(56) References Cited

U.S. PATENT DOCUMENTS

| | | | | |
|---|---|---|---|---|
| 4,456,902 A | * | 6/1984 | Komine | ............... G01N 27/121 204/412 |
| 2006/0065526 A1 | * | 3/2006 | Ono | ................... G01N 27/4071 204/426 |

FOREIGN PATENT DOCUMENTS

| | | |
|---|---|---|
| JP | 4-15057 U | 2/1992 |
| JP | 7-140100 | 6/1995 |
| JP | 10-307115 | 11/1998 |
| JP | 2004-286553 | 10/2004 |
| JP | 2013-213822 | 10/2013 |

OTHER PUBLICATIONS

JPOA—Office Action of Japanese Patent Application No. 2016-041476 dated Jul. 2, 2019 with machine translation.

* cited by examiner

*Primary Examiner* — Daniel S Larkin
*Assistant Examiner* — Anthony W Megna Fuentes
(74) *Attorney, Agent, or Firm* — Fujitsu Patent Center (57) ABSTRACT

A gas sensor device includes: a sensor film including a sensor surface and a resistance which increases with an increase in an amount of gas adsorbed on the sensor surface; a first electrode, a second electrode, and a third electrode that are electrically coupled to the sensor film; and a protective film that covers the sensor surface in a region between the first electrode and the second electrode, wherein the sensor surface is exposed in a region near the third electrode.

15 Claims, 10 Drawing Sheets

GAS SENSOR DEVICE, GAS MEASUREMENT METHOD, AND GAS MEASUREMENT DEVICE

CROSS-REFERENCE TO RELATED APPLICATION

This application is based upon and claims the benefit of priority of the prior Japanese Patent Application No. 2016-041476, filed on Mar. 3, 2016, the entire contents of which are incorporated herein by reference.

FIELD

The embodiments discussed herein are related to a gas sensor device, a gas measurement method, and a gas measurement device.

BACKGROUND

Serious diseases, for example, cancer, are found at earlier stages by screening in order to make early treatment.

The Japanese Laid-open Patent Publication No. 2004-286553, No. 2013-213822, and No. 10-307115 discuss related techniques.

SUMMARY

According to an aspect of the embodiments, a gas sensor device includes: a sensor film including a sensor surface and a resistance which increases with an increase in an amount of gas adsorbed on the sensor surface; a first electrode, a second electrode, and a third electrode that are electrically coupled to the sensor film; and a protective film that covers the sensor surface in a region between the first electrode and the second electrode, wherein the sensor surface is exposed in a region near the third electrode.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

In trying to find, for example, cancer by screening at an earlier stage, marker gas contained in the breath and being specific to the cancer is detected. For instance, ammonia gas as an example of marker gas in relation to pylori infection, which is a risk factor of stomach cancer, and acetaldehyde gas or nonanal gas as an example of marker gas in relation to lung cancer are measured by gas sensor devices.

The gas sensor devices are applied to measure, for example, traces of chemical substances in the breath, such as marker gases specific to various diseases, and so on. The gas sensor device for measuring ammonia gas, for example, includes a CuBr sensor film, and a pair of electrodes that are electrically connected to the CuBr sensor film.

For example, CuBr is used as a material of an ammonia gas sensor that detects a trace of ammonia gas as low as not more than several ppm, for example, in the breath with high sensitivity. When ammonia molecules are adsorbed on a CuBr film, the concentration of $Cu^+$ ions in CuBr is changed in a region where the ammonia molecules are adsorbed, and a resistance value of CuBr, which is a semiconductor, is also changed. The trace of ammonia gas is detected in accordance with the change of the resistance value.

By way of example, the resistance of CuBr in blank gas not containing ammonia gas is measured as a first resistance value. Then, the resistance of CuBr is measured again as a second resistance value after the sensor has been exposed to measurement target gas (breath) containing ammonia gas and after change of the resistance has been stabilized (for example, after the lapse of at least several minutes or longer). Sensing of the presence of ammonia gas or detection (or calculation) of the concentration of the ammonia gas is made in accordance with the change between the two resistance values.

Thus, the blank gas is used, in addition to the measurement target gas, to measure the first resistance value in the blank gas not containing ammonia gas, for example.

In a sensor film having comparatively high sensitivity, such as a film made of CuBr, a fluctuation of background exceeds a certain value in some cases. In those cases, if time is taken from the measurement of the first resistance value to the measurement of the second resistance value, it would be difficult to determine whether the difference between the first resistance value and the second resistance value is caused by the presence of ammonia gas or the fluctuation of the background. Such a difficulty may reduce accuracy in the sensing of the presence of ammonia gas and the detection (or the calculation) of the concentration of the ammonia gas.

As another example, there is proposed a gas sensor device in which one of two sensors is disposed under an environment impermeable to ammonia gas without using the blank gas. In the sensor film having comparatively high sensitivity, such as a film made of CuBr, because a variation of the initial resistance exceeds a certain range, it may be difficult to sense the presence of ammonia gas, or to detect (or calculate) the concentration of the ammonia gas with high accuracy from the difference in resistance between the separate sensor films. It may also be difficult to constitute an environment impermeable to only one of several types of gases.

In one example, a gas sensor device may include a sensor film of which resistance increases with an increase in an amount of gas adsorbed on a sensor surface, at least three electrodes electrically coupled to the sensor film, and a protective film that covers the sensor surface in a region between two of the three electrodes. The sensor surface is exposed in a region near the remaining one of the three electrodes. When the total number of the electrodes is three, for example, a gas measurement device measures a resistance $R_A$ between two of the three electrodes. The gas measurement device further measures a resistance $R_B$ between the remaining one electrode and one of the above-mentioned two electrodes. In the case of $R_A \approx R_B$, the absence of the gas and $R_A < R_B$ are sensed, the presence of the gas is sensed. Moreover, the gas measurement device may determine a resistance ratio $R_B/R_A$, and may calculate a concentration of the gas in accordance with a formula of $C_1 \times (R_B/R_A) - C_2$ by employing values of the constants $C_1$ and $C_2$.

It is to be noted that, in FIG. 1 through FIG. 7, dimensions of various portions, thicknesses of various films, and so on are conveniently illustrated in an exaggerated manner for easier understanding of the drawings, and they may not represent actual dimensions of the various portions, actual thicknesses of the various films, and so on. Thus, in FIG. 1 through FIG. 7, magnitude relations among the dimensions of the various portions and among the thicknesses of the various films may not represent actual magnitude relations.

Figure 1:
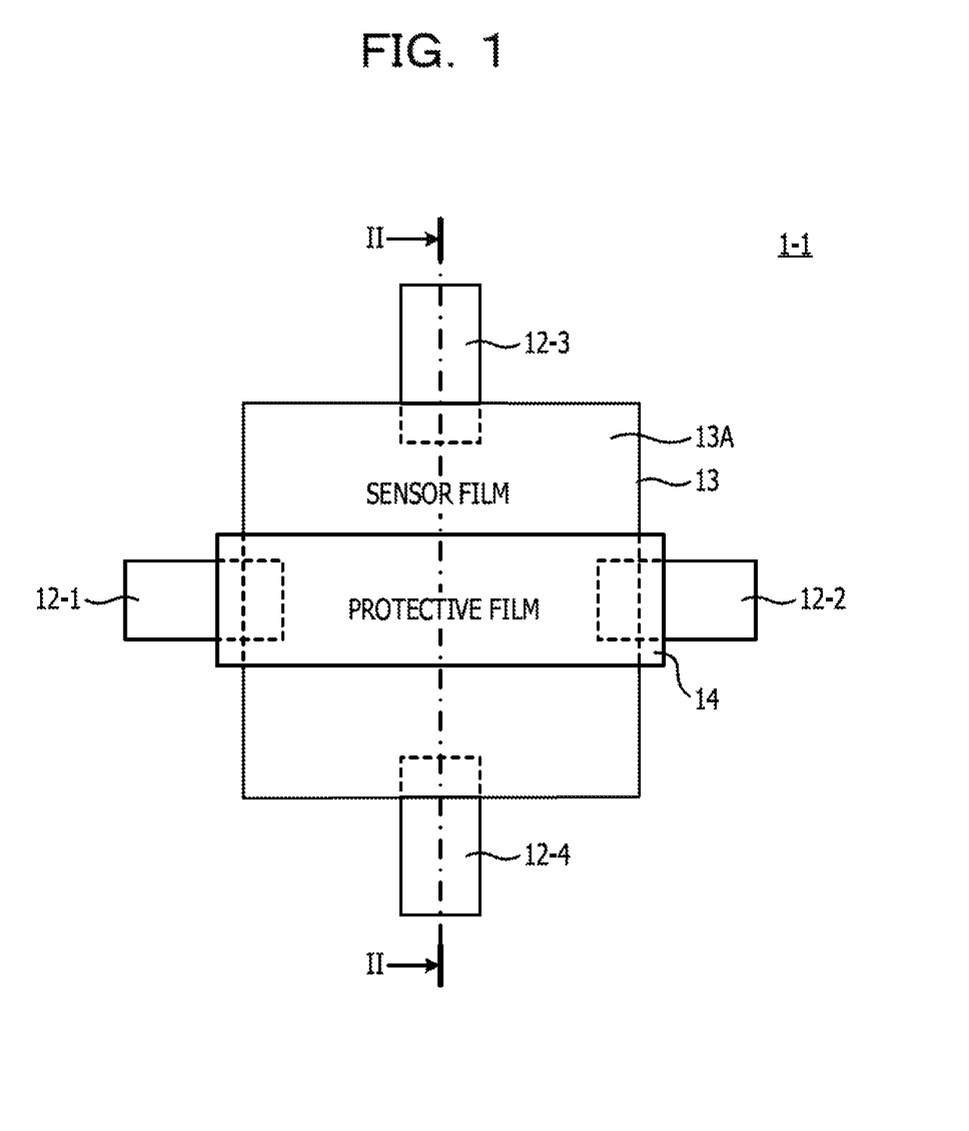
FIG. 1 illustrates an example of a plan view of a gas sensor device.
Figure 2:
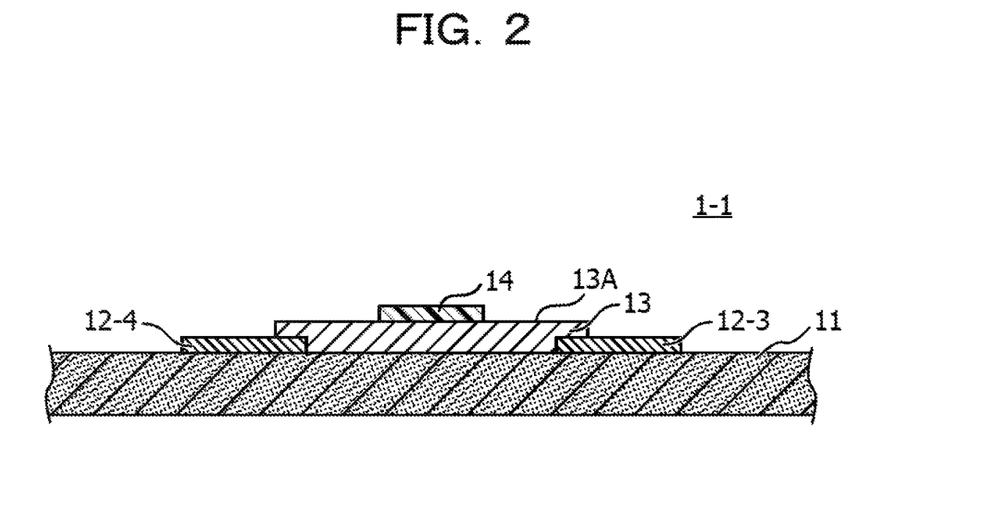
FIG. 2 illustrates an example of a sectional view of a gas sensor device.

FIG. 1 illustrates an example of a plan view of a gas sensor device. FIG. 2 illustrates an example of a sectional view of a gas sensor device. The gas sensor device illustrated in FIG. 2 may be the gas sensor device illustrated in FIG. 1. FIG. 2 is a vertical sectional view taken along a line II-II in FIG. 1.

As illustrated in FIG. 2, a gas sensor device 1-1 includes a substrate 11, first to fourth electrodes 12-1 to 12-4 that are disposed on a surface of the substrate 11, a sensor film 13 that is disposed on the surface of the substrate 11 and surfaces of connection portions at respective fore ends of the first to fourth electrodes 12-1 to 12-4, and that is electrically coupled to the first to fourth electrodes 12-1 to 12-4, and a protective film 14 that is disposed on a sensor surface 13A of the sensor film 13. The connection portions of the first to fourth electrodes 12-1 to 12-4 are disposed to position under the sensor film 13. The substrate 11 is formed of an insulating material, and it may be formed of Si, for example. The first to fourth electrodes 12-1 to 12-4 are each formed of a conductive material, and they may be each formed of a metal or an alloy, for example. The sensor film 13 may be formed of a material that increases the resistance of the sensor film 13 with an increase in an amount of gas, which is a measurement target, adsorbed on the sensor surface 13A. A shape of the sensor film 13 when looked at in a plan view may be rectangular, for example. The protective film 14 is formed of a material acting to suppress adsorption of the gas on the sensor surface 13A that is positioned just under the protective film 14. The protective film 14 may be formed of polyimide, for example. A shape of the protective film 14 when looked at in a plan view may be rectangular, for example.

As illustrated in FIG. 1, of the sensor surface 13A, a region r2 (see FIG. 3) between the first electrode 12-1 and the second electrodes 12-2 is entirely covered with the protective film 14. The protective film 14 covers regions where the connection portions of the first and second electrodes 12-1 and 12-2 overlap the sensor film 13 when looked at in a plan view. In regions r1 and r3 (see FIG. 3) near the third electrode 12-3 and the fourth electrode 12-4, respectively, the protective film 14 is not disposed and the sensor surface 13A is exposed.

When the gas as the measurement target is ammonia gas, the sensor film 13 is formed of any of CuBr, a Cu compound, and an Ag compound. The sensor film 13 may be formed of, for example, a film containing a material selected from CuBr, a Cu compound, and an Ag compound.

Figure 3:
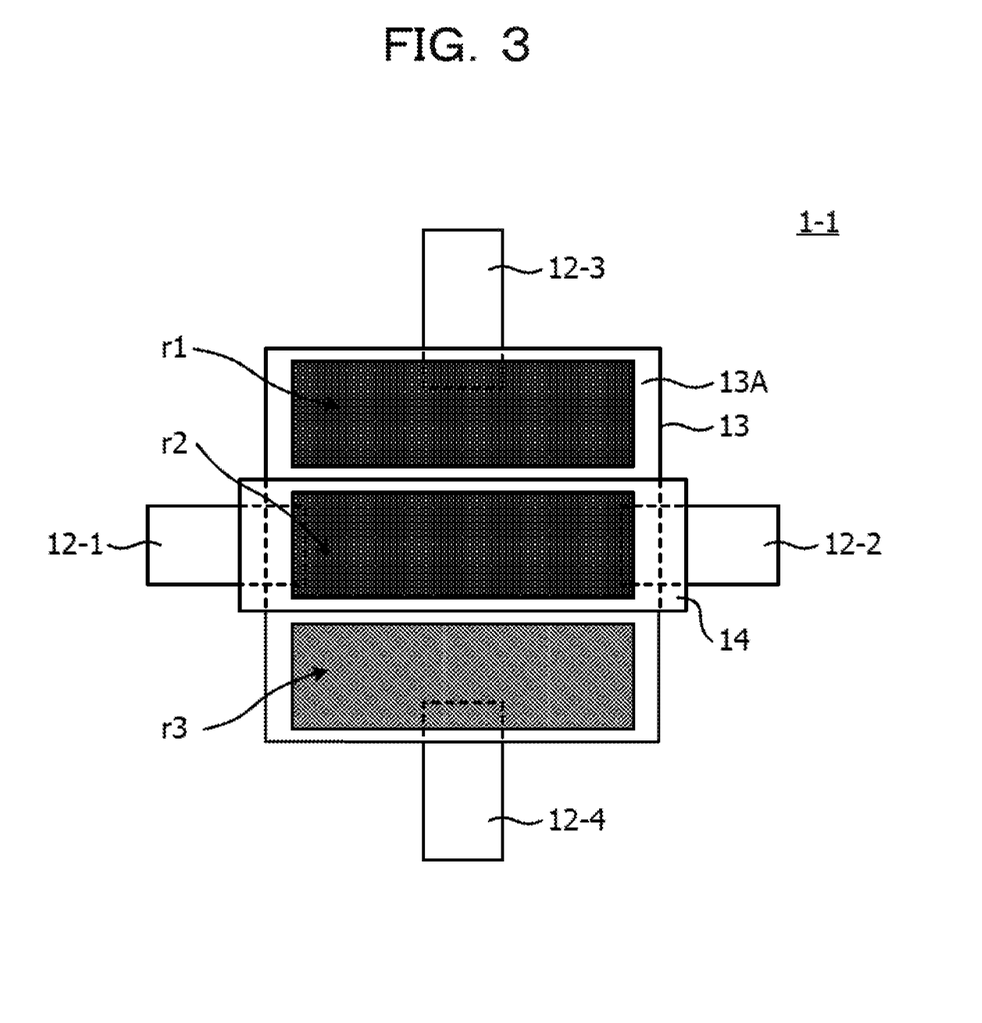
FIG. 3 illustrates an example of a plan view of resistances between electrodes.

FIG. 3 illustrates an example of a plan view of resistances between the electrodes. As illustrated in FIG. 3, the resistance of the region r1 near the third electrode 12-3 is denoted by $R_1$, the resistance of the region r2 between the first electrode 12-1 and the second electrode 12-2 is denoted by $R_2$, and the resistance of the region r3 near the fourth electrode 12-4 is denoted by $R_3$. In this case, a first resistance $R_A$ between the first electrode 12-1 and the second electrode 12-2 is expressed by a formula of $1/R_A = 1/R_1 + 1/R_2 + 1/R_3$. A second resistance $R_B$ between the third electrode 12-3 and the fourth electrode 12-4 is expressed by a formula of $R_B = R_1 + R_2 + R_3$.

In a gas atmosphere containing ammonia gas, the ammonia gas is not adsorbed on the sensor surface 13A that is covered with the protective film 14. The ammonia gas is adsorbed on the sensor surface 13A that is not covered with the protective film 14, and the resistance of the sensor film 13 increases with an increase in an amount of the adsorbed ammonia gas.

As a result of measuring the first resistance $R_A$ between the first electrode 12-1 and the second electrode 12-2 and the second resistance $R_B$ between the third electrode 12-3 and the fourth electrode 12-4, the non-occurrence of absorption of the ammonia gas is sensed in the case of $R_A \approx R_B$ or $R_B/R_A = 1$, and the occurrence of adsorption of the ammonia gas is sensed in the case of $R_A < R_B$ or when $R_B/R_A$ is several tens or several hundreds. The measurement of the first resistance $R_A$ and the measurement of the second resistance $R_B$ may be performed substantially at the same time. Thus, for example, even when background fluctuates, a fluctuation during a short time is as small as negligible. Accordingly, the measurement results of the first resistance $R_A$ and the second resistance $R_B$ may not substantially receive influences. In another example, a resistance ratio $R_B/R_A$ may be further determined, and a concentration of the ammonia gas may be calculated in accordance with the formula of $C_1 \times (R_B/R_A) - C_2$, for example, by employing values of the constants $C_1 = 14.3$ and $C_2 = 104.4$.

Figure 4:
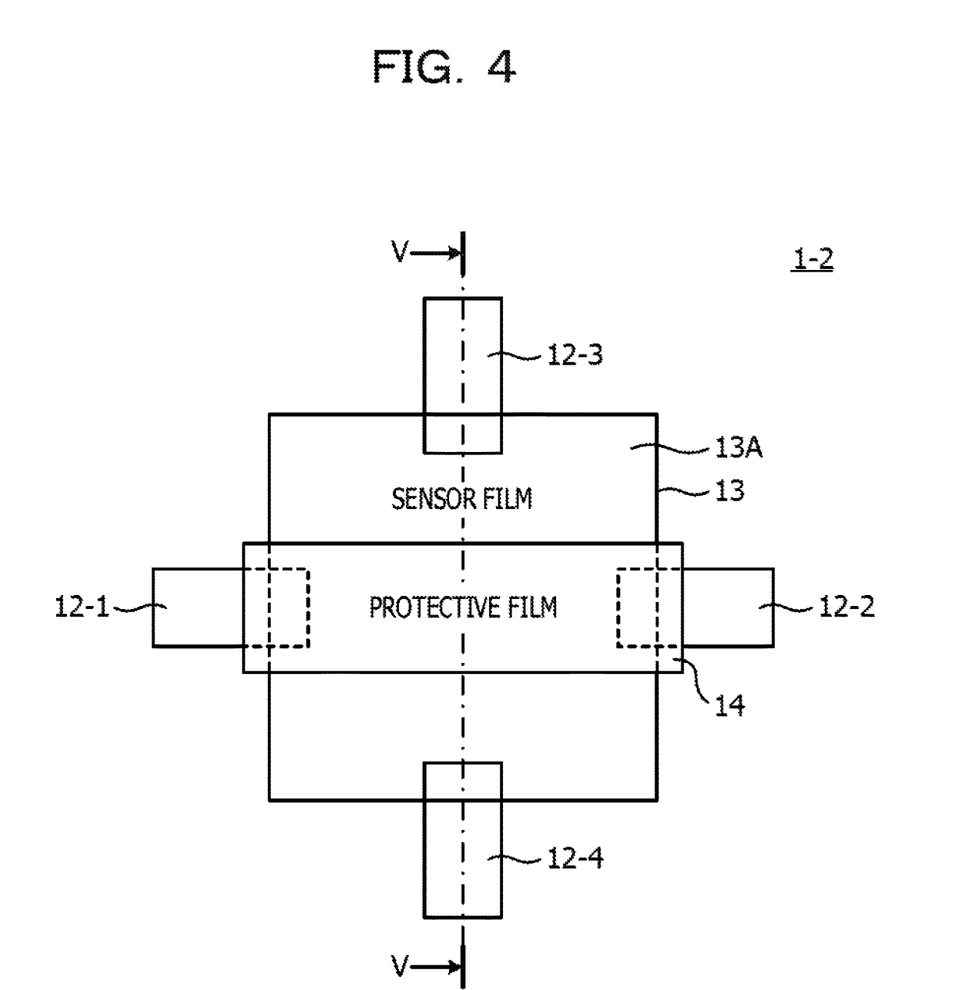
FIG. 4 illustrates an example of a plan view of a gas sensor device.
Figure 5:
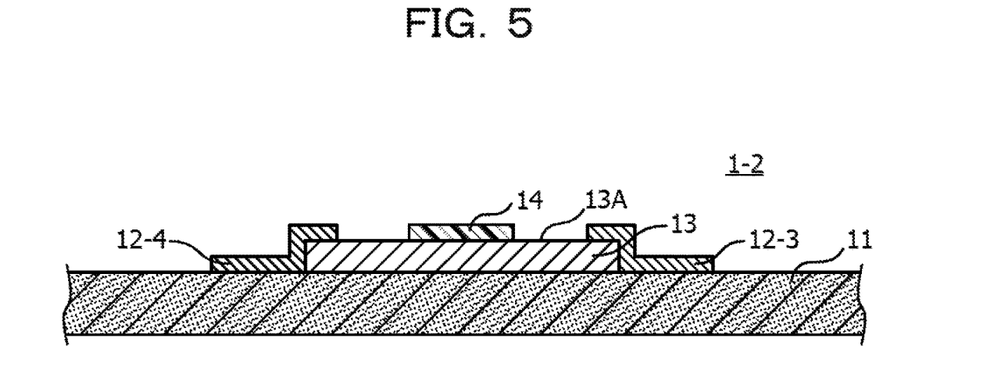
FIG. 5 illustrates an example of a sectional view of a gas sensor device.
Figure 6:
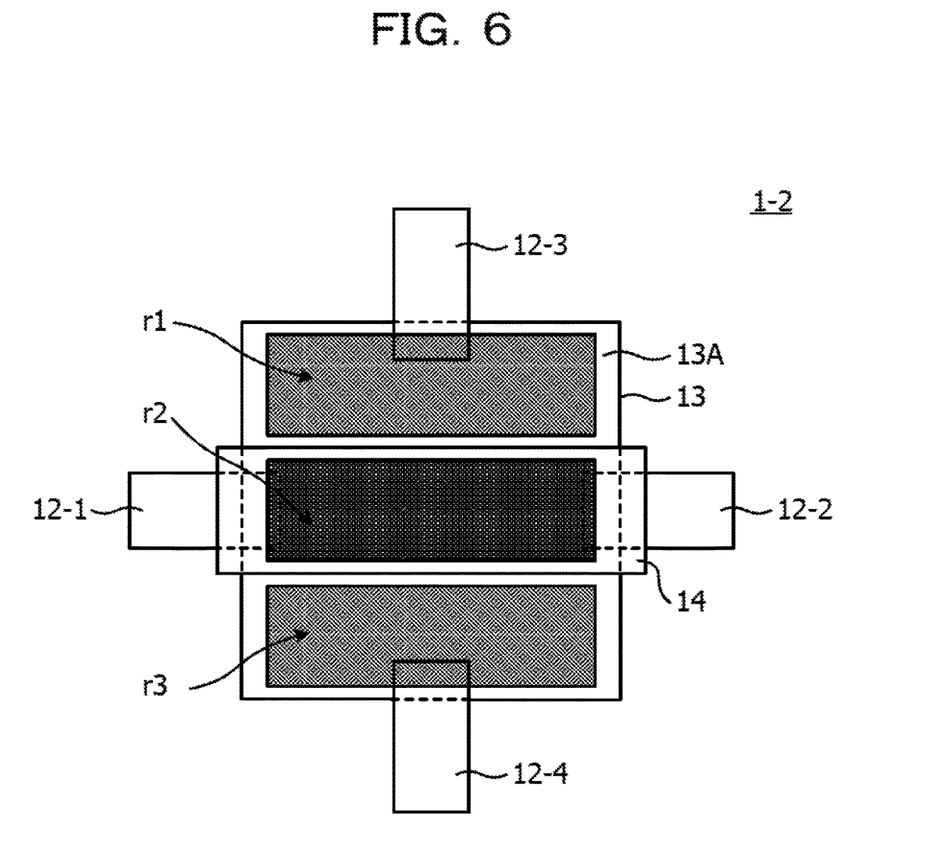
FIG. 6 illustrates an example of a plan view of resistances between electrodes.

As described above, in the gas atmosphere containing the ammonia gas, the one sensor film 13 is divided into a high resistance portion formed by the regions r1 and r3 and a low resistance portion formed by the region r2. Because the first resistance $R_A$ between the two electrodes 12-1 and 12-2, which are coupled to the sensor film 13 covered with the protective film 14, are regarded as a parallel-coupled resistance of the high resistance portion and the low resistance portion in a pseudo-way, the first resistance $R_A$ is not increased even with adsorption of the ammonia gas on the sensor surface 13A. Because the second resistance $R_B$ between the two electrodes 12-3 and 12-4, which are coupled to the sensor film 13 not covered with the protective film 14, are regarded as a series-coupled resistance of the high resistance portion and the low resistance portion, the second resistance $R_B$ is increased with adsorption of the ammonia gas on the sensor surface 13A. Sensing of the presence of the ammonia gas and detection (or calculation) of the concentration of the ammonia gas may be performed in accordance with the difference between the two resistances $R_A$ and $R_B$. Blank gas not containing the ammonia gas may not be used to perform the sensing of the presence of the ammonia gas and the detection (or the calculation) of the concentration of the ammonia gas. FIG. 4 illustrates an example of a plan view of a gas sensor device. FIG. 5 illustrates an example of a sectional view of a gas sensor device. The gas sensor device illustrated in FIG. 5 may be the gas sensor device illustrated in FIG. 4. FIG. 5 is a vertical sectional view taken along a line V-V in FIG. 4. FIG. 6 illustrates an example of a plan view of resistances between electrodes. The same portions in FIG. 4 through FIG. 6 as those in FIG. 1 through FIG. 3 may be denoted by the same reference signs, and description of those portions may be omitted. The first to fourth electrodes 12-1 to 12-4 are disposed on the upper side of the sensor film 13.

Figure 7:
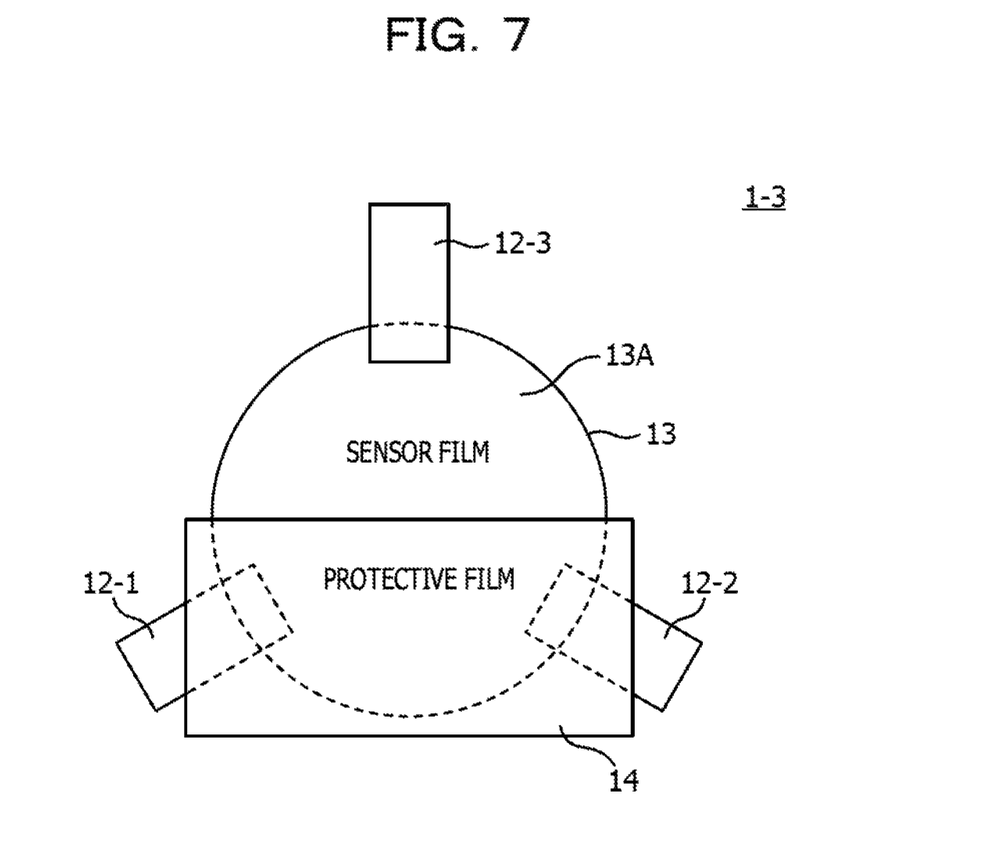
FIG. 7 illustrates an example of a plan view of a gas sensor device.

As illustrated in FIG. 5, in a gas sensor device 1-2, connection portions at respective fore ends of the third and fourth electrodes 12-3 and 12-4 are contacted with the surface of the substrate 11, lateral surfaces of the sensor film 13, and the sensor surface 13A. As illustrated in FIG. 4 and FIG. 6, connection portions at respective fore ends of the first and second electrodes 12-1 and 12-2 are also contacted with the surface of the substrate 11, lateral surfaces of the sensor film 13, and the sensor surface 13A in a similar fashion. FIG. 7 illustrates an example of a plan view of a gas sensor device. The same portions in FIG. 7 as those in FIG. 1 may be denoted by the same reference signs, and description of those portions may be omitted. In FIG. 7, the number of electrodes may be three.

As illustrated in FIG. 7, in a gas sensor device 1-3, the protective film 14 covers the sensor surface 13A of the sensor film 13 in a region between the first electrode 12-1 and the second electrode 12-2. A shape of the sensor film 13 is circular, for example. The protective film 14 covers regions where the connection portions of the first and second electrodes 12-1 and 12-2 overlap the sensor film 13 when looked at in a plan view. In a region near the third electrode 12-3, the sensor surface 13A is exposed. In one example, the sensor film 13 is disposed on the substrate, and connection portions at respective fore ends of the first electrode 12-1, the second electrode 12-2, and the third electrode 12-3 are disposed on the sensor surface 13A of the sensor film 13.

In FIG. 7, as in FIG. 1, the connection portions at respective fore ends of the first electrode 12-1, the second electrode 12-2, and the third electrode 12-3 may be disposed on the substrate, and the sensor film 13 may be disposed on the connection portions of the first electrode 12-1, the second electrode 12-2, and the third electrode 12-3.

With an increase in an amount of the ammonia gas adsorbed on the sensor surface 13A, a second resistance $R_B$ between the first electrode 12-1 and the third electrode 12-3 or a second resistance $R_B$ between the second electrode 12-2 and the third electrode 12-3 is changed to a larger extent than a first resistance $R_A$ between the first electrode 12-1 and the second electrode 12-2. Therefore, as in the gas sensor device illustrated in FIG. 1 through FIG. 3, the non-occurrence of adsorption of the ammonia gas is sensed in the case of $R_A \approx R_B$ or $R_B/R_A \approx 1$, and the occurrence of adsorption of the ammonia gas is sensed in the case of $R_A < R_B$ or when $R_B/R_A$ is several tens or several hundreds. The measurement of the first resistance $R_A$ and the measurement of the second resistance $R_B$ may be performed substantially at the same time. Thus, for example, even when background fluctuates, a fluctuation during a short time is as small as negligible. Accordingly, the measurement results of the first resistance $R_A$ and the second resistance $R_B$ may not substantially receive influences. In another example, a resistance ratio $R_B/R_A$ may be further determined, and a concentration of the ammonia gas may be calculated in accordance with the formula of $C_1 \times (R_B/R_A) - C_2$, for example, by employing values of the constants $C_1 = 14.3$ and $C_2 = 104.4$.

The total number of the electrodes may be at least three. The shape of the electrode is not limited to the rectangular shape. The shape of the sensor film 13 is not limited to the rectangular or circular shape, and it may be elliptic, for example. The shape of the protective film 14 is also not limited to the rectangular shape.

In FIG. 1 through FIG. 7, the sensor film may have a single-layer structure or a multilayer structure.

Depending on the type of a material used for the sensor film, the resistance of the sensor film reduces with an increase in an amount of gas adsorbed on the sensor surface. For example, in the case of employing the sensor film of which resistance reduces with an increase in an amount of the gas adsorbed on the sensor surface, the difference between a resistance ratio $R_B/R_A$ when the gas adsorption does not occur and a resistance ratio $R_B/R_A$ when the gas adsorption occurs may be so small that it is difficult to sense the trace gas based on the resistance ratio $R_B/R_A$.

In FIG. 1 through FIG. 7, by way of example, the resistance of the sensor film increases with an increase in an amount of gas adsorbed on the sensor surface of the sensor film. In the case of employing the sensor film of which resistance increases with an increase in an amount of the adsorbed gas, the difference between a resistance ratio $R_B/R_A$ when the gas adsorption does not occur and a resistance ratio $R_B/R_A$ when the gas adsorption occurs is comparatively large, for example several ten to several hundred times. Hence even the trace gas is easily sensed with high accuracy based on the resistance ratio $R_B/R_A$. Thus, the above-described technique may be applied to a gas sensor device using the sensor film of which resistance increases with adsorption of gas.

The above-described technique may be further applied to a gas sensor device using a sensor film having comparatively high sensitivity, but exhibiting a variation of the initial resistance value or a fluctuation of the background in excess of a certain value. The sensing of gas or the measurement of gas, described above by way of example, is completed in a very short time with use of one sensor film. Accordingly, the above-described technique may be applied to a gas sensor device using a sensor film formed of CuBr, a Cu compound, or an Ag compound which exhibits properties that a carrier concentration in the sensor film is changed with adsorption of gas to be sensed, and that the resistance of the sensor film is changed with the change of the carrier concentration in the sensor film. An example of a manufacturing method for a gas sensor device will be described below. For the sake of convenience in explanation, the following description is made in connection with the case of manufacturing the gas sensor device illustrated in FIG. 1 through FIG. 3.

Four Au electrodes are formed on a Si substrate by an EB (Electron Beam) vapor deposition method. Each of the Au electrodes may have a rectangular shape with dimensions of 2 mm×5 mm and a film thickness of 100 nm, for example. Then, a Cu sensor film is formed on the Si substrate and on the connection portions at respective fore ends of the four Au electrodes by the EB vapor deposition method. The Cu sensor film may have a square shape with dimensions of 15 mm×15 mm and a film thickness of 60 nm, for example. The four Au electrodes are formed to be coupled to, for example, middle zones of four sides of the Cu sensor film, respectively. The Cu sensor film is immersed in a solution of $CuBr_2$ appropriately to perform a process of forming CuBr. A polyimide protective film having a width of 5 mm is formed on the sensor film in a region between a pair of opposing two among the four Au electrodes. At that time, a region of a CuBr sensor surface of the sensor film, the region being positioned between the pair of opposing Au electrodes, is entirely covered with the polyimide protective film.

Figure 8:
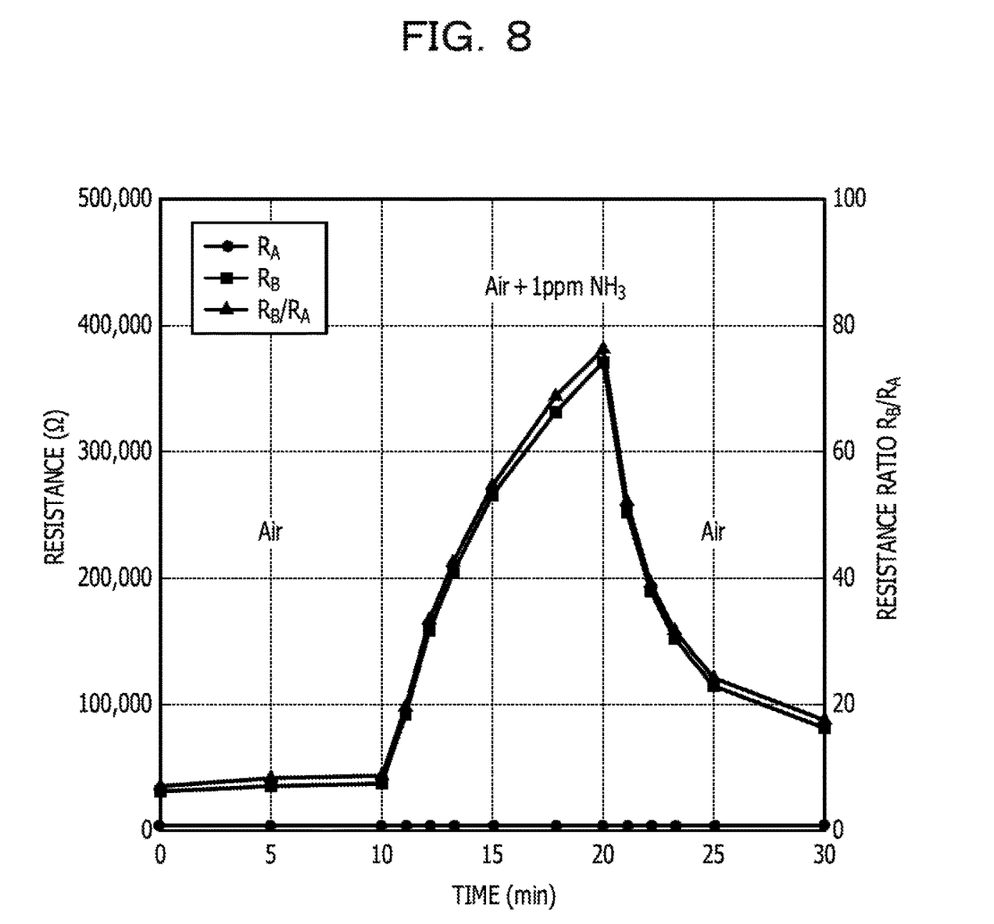
FIG. 8 plots examples of resistance change in a sensor film of a gas sensor device.

FIG. 8 plots examples of resistance change in a sensor film of a gas sensor device. The gas sensor device used to obtain plots in FIG. 8 may be manufactured in accordance with the above-described method. In FIG. 8, a mark ● denotes the plot of the first resistance $R_A$, a mark ■ denotes the plot of the second resistance $R_B$, and a mark ▲ denotes the plot of the resistance ratio $R_B/R_A$. In FIG. 8, the vertical axis on the left side represents resistance values (Ω) of the first resistance $R_A$ and the second resistance $R_B$, and the vertical axis on the right side represents the resistance ratio $R_B/R_A$. The horizontal axis represents time (minute).

With use of the gas sensor device manufactured as described above, for example, the first resistance $R_A$ between the one pair of Au electrodes in the region where the polyimide protective film is formed, and the second resistance $R_B$ between the remaining one pair of Au electrodes are continuously measured in a gas atmosphere (Air+1 ppm $NH_3$) containing 1 ppm of ammonia gas. As plotted in FIG. 8, the measurement results are $R_A$=4.8 kΩ, $R_B$=370.4 kΩ, and the resistance ratio $R_B/R_A$=77.2.

With use of the same gas sensor device as that used above, the first resistance $R_A$ and the second resistance $R_B$ are continuously measured in a gas atmosphere (Air) not containing ammonia gas. The measurement results are $R_A$=4.4 kΩ, $R_B$=32.0 kΩ, and the resistance ratio $R_B/R_A$=7.3.

Thus, the resistance ratio $R_B/R_A$ differs at least 10 times or more (for example, several ten to several hundred times) depending on whether 1 ppm of ammonia gas is present in the gas atmosphere or not, and the presence of the ammonia gas is sensed evidently.

The relation between the concentration of the ammonia gas and the resistance ratio $R_B/R_A$ is determined, for example, in accordance with the above-mentioned formula. The concentration (ppb) of the ammonia gas is calculated using $C_1 \times (R_B/R_A) - C_2 = 14.3 \times (R_B/R_A) - 104.4$.

In one example, the first resistance $R_A$ and the second resistance $R_B$ are continuously measured in a gas atmosphere containing 500 ppb of ammonia gas, and the resistance ratio $R_B/R_A$=43.7 is obtained.

In accordance with the above-mentioned formula, the concentration (ppb) of the ammonia gas is determined as $14.3 \times 43.7 - 104.4 = 520.5$ (ppb). Thus, quantitative determination of the concentration of the ammonia gas is performed.

The first resistance $R_A$ and the second resistance $R_B$ are continuously measured in a gas atmosphere where the concentration of the ammonia gas is unknown, and the resistance ratio $R_B/R_A$=66.3 is obtained. The concentration (ppb) of the ammonia gas is calculated in accordance with the above-mentioned formula, and $14.3 \times 66.3 - 104.4 = 843.7$ (ppb) is obtained.

Figure 9:
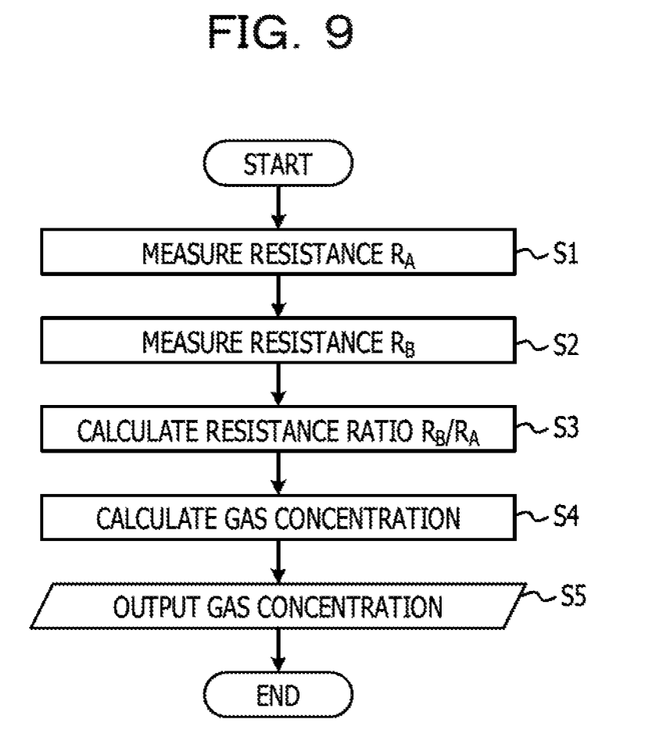
FIG. 9 illustrates an example of a gas measurement method.

FIG. 9 illustrates an example of a gas measurement method. The gas measurement method illustrated in FIG. 9 may be executed by a computer (or a processor), for example.

Figure 10:
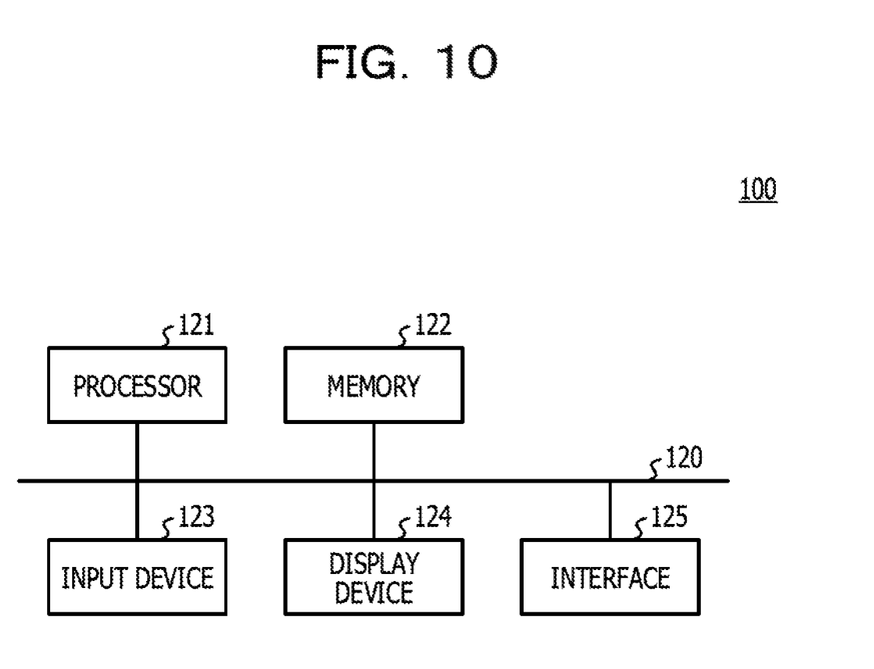
FIG. 10 illustrates an example of a computer.

FIG. 10 illustrates an example of a computer. A computer 100 illustrated in FIG. 10 includes a processor 121, a memory 122, an input device 123, a display device 124, and an interface (or a communication device) 125, which are interconnected via a bus 120. The processor 121 may include a CPU (Central Processing Unit), for example, and it supervises entire control of the computer 100 by running programs stored in the memory 122. The memory 122 may include, for example, a semiconductor storage device, a magnetic recording medium, an optical recording medium, or a magneto-optical recording medium. The memory 122 stores various programs including a gas measurement program to be run by the processor 121, various data, and so on.

The input device 123 may include, for example, a keyboard that is operated by a user (or an operator). The input device 123 is used to input commands and data to the processor 121. The display device 124 displays messages to the user, the gas sensing result obtained with a gas measurement process, the calculated result of the gas concentration, and so on. The interface 125 inputs the resistance between the electrodes, which is output from the gas sensor device, to the computer 100.

A configuration of the computer 100 is not limited to a hardware configuration in which the components of the computer 100 are interconnected via the bus 120.

In FIG. 9, when the gas measurement process is started, the processor 121 measures, in operation S1, the first resistance $R_A$ between the first and second electrodes 12-1 and 12-2 of the gas sensor device 1-1 illustrated in FIG. 1 through FIG. 3, for example. In operation S2, the processor 121 measures the second resistance $R_B$ between the third and fourth electrodes 12-3 and 12-4 of the gas sensor device 1-1. The measurement in the operation S1 and the measurement in the operation S2 may be executed substantially at the same time in a continuous manner. Because the measurements in the operations S1 and S2 are executed substantially at the same time, the order in executing the operation S1 and the operation S2 may be exchanged in FIG. 9.

In operation S3, the processor 121 calculates the resistance ratio $R_B/R_A$ from the first resistance $R_A$ and the second resistance $R_B$ both obtained with the measurement. In operation S4, the processor 121 calculates the concentration of the measurement target gas from the calculated resistance ratio $R_B/R_A$. Because the measurement target gas is ammonia gas, for example, the processor 121 calculates, in the operation S4, the concentration (ppb) of the ammonia gas in accordance with $C_1 \times (R_B/R_A) - C_2$, for example, from the calculated resistance ratio $R_B/R_A$. In operation S5, the processor 121 displays the calculated result of the gas concentration on the display device 124. The gas measurement process is thereby ended.

By way of example, the absence of the gas is sensed in the case of $R_A \approx R_B$, and the presence of the gas is sensed in the case of $R_A < R_B$. Accordingly, in the operation S5, the processor 121 may display the gas sensing result on the display device 124 from the first resistance $R_A$ and the second resistance $R_B$ both obtained with the measurement.

The processor 121 may be one example of a gas measurement device for executing the above-described gas measurement process. In that case, the gas measurement device may be a gas sensor device including a sensor film of which resistance increases with an increase in an amount of gas adsorbed on a sensor surface, a first electrode, a second electrode, and a third electrode that are electrically coupled to the sensor film, and a protective film that covers the sensor surface in a region between the first electrode and the second electrode, the sensor surface being exposed in a region near the third electrode. The gas measurement device may include a first measurement unit that measures a resistance $R_A$ between the first electrode and the second electrode, a second measurement unit that measures a resistance $R_B$ between the first electrode or the second electrode and the third electrode, and a sensing unit that senses the absence of the gas in the case of $R_A \approx R_B$ and the presence of the gas in the case of $R_A < R_B$.

According to the gas sensor device, the gas measurement method, and the gas measurement device described above, the gas may be sensed with high accuracy. Since the gas is sensed without using blank gas, the gas may be sensed with high accuracy in a short time. Sensing of the presence of trace gas or detection (or calculation) of the concentration of the trace gas may be performed with high accuracy.

According to the gas sensor device, the gas measurement method, and the gas measurement device described above, sensing and quantitative determination of gas, such as a trace of ammonia gas, are performed without using blank gas. The sensing and the quantitative determination of the gas are performed even with use of a sensor film, such as a CuBr film, having properties that the difference in initial resistance among individual films and a fluctuation of background which is larger than a certain value although sensitivity is comparatively high. When the gas sensor device is used, for example, as a sensor for disease marker gas that is contained in the breath, it may be possible to improve the accuracy in screening for cancer and so on, to develop applications of the gas sensor device to a field of follow-up at home, and to enhance contribution to the aging society where the medical care cost increases.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A gas sensor device comprising: a sensor film, which is a film containing one of CuBr, a Cu compound, and an Ag compound, including a sensor surface and a resistance which increases with an increase in an amount of ammonia gas adsorbed on the sensor surface; a first electrode, a second electrode, and a third electrode that are electrically coupled to the sensor film; and a protective film that covers the sensor surface in a region between the first electrode and the second electrode, wherein the sensor surface is exposed in a region adjacent to the third electrode.

2. The gas sensor device according to claim 1, further comprising a fourth electrode, wherein the sensor surface is exposed in a region adjacent to the fourth electrode.

3. The gas sensor device according to claim 2, wherein the sensor surface has a rectangular shape, the first electrode and the second electrode are connected to a first pair of opposing sides of the rectangular shape, and the third electrode and the fourth electrode are connected to a second pair of opposing sides of the rectangular shape.

4. The gas sensor device according to claim 2, wherein a resistance between the third electrode and the fourth electrode makes a lamer change than a resistance between the first electrode and the second electrode with the increase in the amount of the ammonia gas adsorbed on the sensor surface.

5. The gas sensor device according to claim 1, further comprising a substrate that contains an insulating material, wherein the first electrode, the second electrode, and the third electrode are disposed on the substrate, and the sensor film is disposed on the first electrode, the second electrode, and the third electrode.

6. The gas sensor device according to claim 1, further comprising a substrate that contains an insulating material, wherein the sensor film is disposed on the substrate, and the first electrode, the second electrode, and the third electrode are disposed on the sensor film.

7. The gas sensor device according to claim 1, wherein a resistance between the first electrode and the third electrode and a resistance between the second electrode and the third electrode make a larger change than a resistance between the first electrode and the second electrode with the increase in the amount of the ammonia gas adsorbed on the sensor surface.

8. A gas measurement method comprising: measuring, with use of a gas sensor device including a sensor film which is a film containing one of CuBr, a Cu compound, and an Ag compound and of which resistance increases with an increase in an amount of ammonia gas adsorbed on a sensor surface, a first electrode, a second electrode, and a third electrode that are electrically coupled to the sensor film, and a protective film that covers the sensor surface in a region between the first electrode and the second electrode, the sensor surface being exposed in a region adjacent to the third electrode, a resistance $R_A$ between the first electrode and the second electrode; measuring, with use of the gas sensor device, a resistance $R_B$ between the first electrode or the second electrode and the third electrode; sensing absence of the ammonia gas in case of $R_A \approx R_B$; and sensing presence of the ammonia gas in case of $R_A < R_B$.

9. The gas measurement method according to claim 8, further comprising: determining a resistance ratio $R_B/R_A$; and calculating a concentration of the ammonia gas in accordance with a formula of $C_1 \times (R_B/R_A) - C_2$ by employing values of constants $C_1$ and $C_2$ which are respective predetermined values to calculate the concentration of the ammonia gas.

10. The gas measurement method according to claim 9, wherein the respective predetermined values of the constants $C_1$ and $C_2$ are 14.3 and 104.

11. The gas measurement method according to claim 8, wherein a measurement of the resistance $R_A$ and a measurement of the resistance $R_B$ are performed substantially at the same time.

12. A gas measurement device comprising: a memory that stores a gas measurement program; and a processor that performs, based on the gas measurement program, operations of: measuring, with use of a gas sensor device including a sensor film which is a film containing one of CuBr, a Cu compound, and an Ag compound and of which resistance increases with an increase in an amount of ammonia gas adsorbed on a sensor surface, a first electrode, a second electrode, and a third electrode that are electrically coupled to the sensor film, and a protective film that covers the sensor surface in a region between the first electrode and the second electrode, the sensor surface being exposed in a region adjacent to the third electrode, a resistance $R_A$ between the first electrode and the second electrode; measuring, with use of the gas sensor device, a resistance $R_B$ between the first electrode or the second electrode and the third electrode; sensing absence of the ammonia gas in case of $R_A \approx R_B$; and sensing presence of the ammonia gas in case of $R_A < R_B$.

13. The gas measurement device according to claim 12, wherein the processor:
determines a resistance ratio $R_B/R_A$; and
calculates a concentration of the ammonia gas in accordance with a formula of $C_1 \times (R_B/R_A) - C_2$ by employing values of constants $C_1$ and $C_2$ which are respective predetermined values to calculate the concentration of the ammonia gas.

14. The gas measurement device according to claim 13, wherein the respective predetermined values of the constants $C_1$ and $C_2$ are 14.3 and 104.

15. The gas measurement device according to claim 12, wherein a measurement of the resistance $R_A$ and a measurement of the resistance $R_B$ are performed substantially at the same time.

* * * * *